United States Patent [19]

Jautelat

[11] Patent Number: 5,612,483
[45] Date of Patent: Mar. 18, 1997

US005612483A

[54] PROCESS FOR THE PREPARATION OF NITRO-SUBSTITUTED ARYLAMINES

[75] Inventor: Manfred Jautelat, Burscheid, Germany

[73] Assignee: Bayer Aktiengesellschaft, Leverkusen, Germany

[21] Appl. No.: 523,970

[22] Filed: Sep. 6, 1995

[30] Foreign Application Priority Data

Sep. 13, 1994 [DE] Germany .................. 44 32 556.8

[51] Int. Cl.$^6$ ............... C07C 209/12; C07D 239/42; C07D 213/74

[52] U.S. Cl. ............ 544/332; 544/321; 546/160; 546/312; 548/130; 548/197; 548/559; 549/68; 549/481; 558/418; 562/435; 564/408

[58] Field of Search ............ 564/408; 558/418; 562/435; 544/321, 332; 546/312

[56] References Cited

U.S. PATENT DOCUMENTS 5,117,063  5/1992  Stern et al. ................ 564/398
5,252,737  10/1993  Stern et al. ................ 544/392

FOREIGN PATENT DOCUMENTS 0566783  10/1993  European Pat. Off. .
9324447  12/1993  WIPO .

OTHER PUBLICATIONS

Ber. Deutsch. Chem. Gesellschaft. 1903, 36, 4135–4138.

M.K. Stern, et al., J. Am. Chem. Soc., vol. 114, No. 23, pp. 9237–9238, (1992).

N.R. Ayyangar, et al., Tetrahedron Letters, vol. 31, No. 22, pp. 3217–3220, (1990).

*Primary Examiner*—Richard L. Haymond
*Attorney, Agent, or Firm*—Sprung Horn Kramer & Woods

[57] ABSTRACT

Nitro-substituted aromatics can be directly aminated with amines in the presence of simple bases and oxygen.

8 Claims, No Drawings

PROCESS FOR THE PREPARATION OF NITRO-SUBSTITUTED ARYLAMINES

The invention relates to a process for the preparation of nitro-substituted arylamines from nitroaromatics, amines and oxygen in the presence of bases.

Aromatic amines are important intermediates for the production of dyes, plant protection agents, pharmaceuticals and for the photographic industry.

Industrially important processes for the preparation of aromatic amines are the reduction of nitro groups in easily accessible nitroaromatics or the reaction of halogenoaromatics with ammonia or amines. Although these processes are utilized industrially to great extents, unsatisfactory yields often result because of the multi-step reaction. The direct amination of nitrobenzene with acetanilide in the presence of bases in DMSO is also known, p-nitrosodiphenylamine being formed as the main product (Tetrahedron Lett. 1990, 22, 3217–3220). A process for the preparation of N-aliphatically substituted p-phenylene-diamines by reaction of nitrobenzene with aliphatic amines in the presence of base and proton-containing substances is furthermore described (U.S. Pat. No. 5,252,737). In addition, a process for the preparation of p-nitroaromatic amides and amines is known which comprises the reaction of nitrobenzene with amides or amines without oxidizing agents in the presence of specific bases, such as tetraalkylammonium hydroxides, in the presence of proton-containing substances (WO 93/24447, U.S. Pat. No. 5,117,063 and J. Am. Chem. Soc. 1992, 114, 9237). These processes require specific conditions or bases and/or give yields which are not always satisfactory.

Surprisingly, a generally applicable process for the direct amination of nitro-substituted aromatics with amines in the presence of simple bases and oxygen has now been found. The reactions lead in good yields to the corresponding amines.

The invention relates to a process for the preparation of aromatic amines of the formula

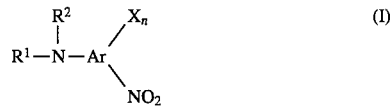

wherein

Ar denotes a mono- or polycyclic, preferably mono- or bicyclic, aromatic radical having 4 to 16 C atoms, which can also contain 1 to 2 heteroatoms from the series consisting of N, O and S, $R^1$ denotes a mono- or polycyclic, preferably mono- or bicyclic, aromatic radical having 5 to 16 ring members, which consist of carbon atoms and optionally up to 3 heteroatoms from the series N, O and S, $R^2$ denotes hydrogen, $C_1$–$C_8$-alkyl, $C_2$–$C_8$-alkenyl, $C_3$–$C_7$-cycloalkyl or $C_6$–$C_{14}$-aryl, where these substituents can be substituted 1 to 3 times by halogen, $C_1$–$C_4$-alkyl, amino and/or $C_1$–$C_4$-alkoxy, X denotes halogen, cyano, $C_1$–$C_4$-alkyl, halogenated $C_1$–$C_4$-alkyl, $C_1$–$C_4$-alkoxy, halogenated $C_1$–$C_4$-alkoxy, $C_1$–$C_4$-alkylmercapto, halogenated $C_1$–$C_4$-alkylmercapto, $C_1$–$C_4$-alkylsulphonyl, carboxyl or nitro, n denotes zero, 1, 2 or 3, preferably zero, 1 or 2, where if n>1 the substituents X can be different, according to which nitroaromatics of the formula

wherein X, Ar and n have the meanings indicated above, are reacted with amines of the formula

wherein $R^1$ and $R^2$ have the meanings indicated above, in the presence of bases using oxygen in polar solvents.

Preferred aromatic $C_4$–$C_{16}$-radicals Ar include, for example, benzene, naphthalene, pyridine, quinoline and thiophene radicals, preferably benzene and naphthalene radicals.

Aromatic radicals $R^1$ having 5–16 ring members include, for example, pyrazole, imidazole, 1,2,4-triazole, thiazole, benzene, naphthalene, pyridine, quinoline, pyrimidine and thiophene radicals.

"$C_1$–$C_8$-Alkyl" and "$C_1$–$C_4$-alkyl" include linear and branched radicals such as methyl, ethyl, isopropyl and n-, sec- and tert-butyl.

"$C_2$–$C_8$-Alkenyl" includes vinyl and allyl.

"$C_3$–$C_7$-Cycloalkyl" includes cyclopropyl, cyclopentyl and cyclohexyl.

"$C_6$–$C_{14}$-Aryl" represents unsubstituted aryl radicals such as phenyl or naphthyl which can be substituted one or more times by halogen, $C_1$–$C_6$-alkyl, nitro, amino, $C_1$–$C_6$-alkoxy, $C_1$–$C_6$-alkylthio, sulpho acid, hydroxyl, formyl, benzoyl, carboxyl, cyano, phenyl and phenyl-$C_1$14 $C_6$-alkyl.

"Halogen" represents bromine or iodine, preferably fluorine and chlorine.

"Halogenated $C_1$–$C_4$-alkyl" includes, e.g., trifluoromethyl and dichlorofluoromethyl.

"$C_1$–$C_4$-Alkoxy" preferably denotes methoxy; "halogenated $C_1$–$C_4$-alkoxy" preferably represents trifluoromethoxy.

"$C_1$–$C_4$-Alkylmercapto" preferably denotes methylmercapto; "halogenated $C_1$–$C_4$-alkylmercapto" preferably represents trifluoromethylmercapto.

"$C_1$–$C_4$-Alkylsulphonyl" preferably represents methylsulphonyl.

Preferred nitroaromatics (II) include, for example, nitrobenzene, m-chloronitrobenzene, m-nitrobenzonitrile, m-trifluoromethylnitrobenzene, 3-fluoro-nitrobenzene, 3-nitrotoluene, 3-trifluoromethoxynitrobenzene, 3-trifluoromethylthio-nitrobenzene, 3,5-dichloronitrobenzene, 2-nitrobenzonitrile, 2-nitrobenzoic acid, 1-nitronaphthalene, 2-nitronaphthalene, 2-nitrothiophene, 3-nitrothiophene, 2-nitrofuran, N-alkylated and N-arylated 2-and 3-nitropyrroles, 2-, 3- and 4-nitro-pyridine, 4-ethoxy-3-nitropyridine and 5-, 6- and 8-nitroquinoline.

Preferred amines of the formula (III) include, for example, aniline, N-methylaniline, N-butylaniline, N-isobutylaniline, diphenylamine, 2-chloroaniline, 2,4-dichloroaniline, 2,6-dichloroaniline, 2,4,6-trichloroaniline, 3-nitroaniline, 4-nitroaniline, N-cyclohexyl-4-nitroaniline, 4-chloro-2-nitroaniline, 2,6-dichloro-4-nitroaniline, 2-bromo-4-nitroaniline, 3-methylaniline, 4-chloro-2-trifluoromethylaniline, 3-trifluoromethylaniline, N-butyl-3-methylaniline, 3,5-dimethylaniline, 3,5-bis-trifluoromethylaniline, 4-aminobiphenyl, 1-naphthylamine, 1-aminopyrene, 3-aminodibenzofuran, 2-aminopyridine, 2-amino-4,6-dimethylpyrimidine, 2-amino-4-methoxy-6-methylpyrimidine, 2-amino-4,6-dimethyl-1,3,5-triazine, 1-amino- 1,3,4-triazole, 2-aminothiazole, 5-amino-3-phenyl- 1,2,4-thiadiazole.

Suitable bases are both organic and inorganic bases; inorganic bases are preferred, such as, e.g., alkali metal hydroxides, alkali metal amides, alkali metal alkoxides or alkali metal hydrides. Alkali metal hydroxides are particularly preferred, such as, e.g., lithium hydroxide, sodium hydroxide, potassium hydroxide, caesium hydroxide and potassium tert-butoxide. The bases are preferably employed in the form of powders or microgranules (micropills).

Oxygen can be employed as a pure gas or particularly preferably in mixtures with other gases, for example in the form of air.

Suitable solvents for the preparation of the compounds (I) according to the invention include organic and inorganic solvents. Preferred organic solvents are polar aprotic solvents, such as, for example, dimethyl sulphoxide, dimethylformamide, N-methylpyrrolidone, pyridine, dioxane, THF, acetonitrile, sulpholane, dimethyl sulphone and their mixtures. A preferred inorganic solvent is, for example, liquid ammonia. Small amounts, i.e. up to 10% by weight, based on total solvent, of proton-containing solvents, such as, for example, water, are acceptable. The preferred solvent is dimethyl sulphoxide.

The reaction can be carried out within a wide temperature range. In general, it is carried out at temperatures between −35° C. and 120° C., preferably between 20° C. and 100° C., more preferably between 20° and 80° C.

When carrying out the process according to the invention, it is in general carried out under normal pressure; however, it is also possible to work at elevated or reduced pressure.

When carrying out the process according to the invention, 0.5 to 10 mol, preferably 0.7 to 2 mol, of amines of the formula (III) and also 1 to 10 equivalents, preferably 2 to 6 equivalents, of base are in general employed relative to 1 mol of the nitroaromatic of the formula (II). Oxygen is preferably passed in undiluted or diluted in an excess.

If 3-nitrobenzotrifluoride, aniline and air are used as starting substances and sodium hydroxide as the base, the course of the process for the preparation of nitro-substituted amines can be represented by the following equation:

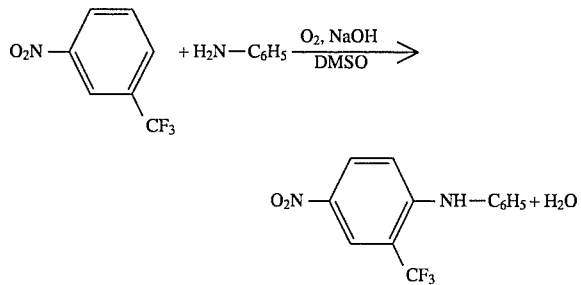

The starting substances of the formulae (II) and (III) are known or can be prepared by known processes.

Working up can be carried out by the customary methods. In general, a procedure is used in which the reaction mixture is strongly diluted with water and the reaction product which is deposited is separated off and isolated, or the mixture is diluted with water and extracted with a poorly water-miscible organic solvent. The product is isolated from the organic phase after this has been dried and concentrated.

EXAMPLES

Example 1

2-(4-Nitro-2-trifluoromethylphenyl-amino)-pyridine 1.91 g (10 mmol) of 3-nitrobenzotrifluoride, 1.88 g (20 mmol) of 2-aminopyridine and 1.2 g (30 mmol) of sodium hydroxide in the form of microbeads are heated at 50° C. for 6 h in 30 ml of abs. DMSO while passing through dry air. After cooling, the mixture is diluted with ethyl acetate and extracted several times by shaking with water. After drying and stripping off the organic solvent, 3.8 g of crude product are obtained which is purified by chromatography on silica gel using petroleum ether and ethyl acetate (volume ratio 1:1). 2.3 g (8.1 mmol, 81%) of 2-(4-nitro-2-trifluoromethylphenylamino)-pyridine of m.p. 83°–84° C. are thus obtained.

Example 2

1-(4-Chloro-2-trifluoromethylphenyl)-amino-4-nitro-2-trifluoromethylbenzene 1.91 g (10 mmol) of 3-nitrobenzotrifluoride, 1.96 g (10 mmol) of 4-chloro-2-trifluoromethylaniline and 1.2 g (30 mmol) of NaOH micropills are heated at 50° C. for 24 h in 30 ml of abs. DMSO while passing dry air over. Working up using ethyl acetate and saturated, aqueous sodium carbonate solution leads to 3.8 g (10 mmol, 100%) of the above product, which after chromatographic purification on silica gel using petroleum ether/ethyl acetate (volume ratio 10:1) has an m.p. of 84°–85° C.

Example 3

N-Methyl-N-(4-nitro-2-trifluoromethylphenyl)-aniline 1.91 g (10 mmol) of 3-nitrobenzotrifluoride, 1.09 g (10 mmol) of N-methylaniline and 1.2 g (30 mmol) of NaOH micropills are added at −40° C. to 40 ml of liquid ammonia. Dried air is then passed through and the mixture is stirred under $NH_3$ reflux for 4 h. After the evaporation of ammonia, the residue is diluted with saturated, aqueous sodium carbonate solution and extracted several times by shaking with ethyl acetate. 3.0 g of crude product remain from the organic phase after drying and stripping off the solvent. By chromatography on silica gel using petroleum ether/ethyl acetate (volume ratio 9:1), 1.2 g (4.1 mmol, 41%) of N-methyl-N-(4-nitro-2-trifluoromethylphenyl)aniline are isolated.

The following compounds are prepared according to Examples 1 to 3:

| No. | Product | Physical data |
|---|---|---|
| 4 | 4-O₂N, 2-CF₃ phenyl—NH—C₆H₅ | m.p. 51–52° C. |
| 5 | 4-O₂N, 2-CF₃ phenyl—NH—C₆H₄—4-NO₂ | m.p. 119–121° |
| 6 | 4-O₂N, 2-CF₃ phenyl—NH—(pyrimidin-2-yl) | m.p. 104–107 |
| 7 | 4-O₂N, 2,6-(CF₃)₂ phenyl—NH—C₆H₅ | 351 (M + H⁺) |
| 8 | 4-O₂N, 2-CF₃ phenyl—NH—(4,6-dimethylpyrimidin-2-yl) | 313 (M + H⁺) |
| 9 | 4-O₂N, 3-NO₂, 6-COOH phenyl—NH—C₆H₅ | 302 (M − H⁺) |
| 10 | 4-O₂N, 2-CF₃ phenyl—NH—(4,6-dimethoxypyrimidin-2-yl) | 345 (M + H⁺)<br>m.p. 158–160° C. |
| 11 | 4-O₂N, 2,6-Cl₂ phenyl—NH—(2-CF₃, 4-Cl phenyl) | 385 (M + H⁺)<br>m.p. 98–100° C. |
| 12 | 4-O₂N, 2,6-Cl₂ phenyl—NH—(pyrimidin-2-yl) | m.p. 205–207° C. |

| No. | Product | Physical data |
|-----|---------|---------------|
| 13 | 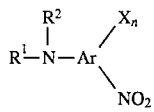 | 250 (M + H⁺) |
| 14 |  | 317 (M + H⁺) |
| 15 | 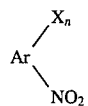 | 215 (M + H⁺) m.p. 129–132° C. |

I claim:

1. Process for the preparation of compounds of the formula $$R^1-\underset{\underset{R^2}{|}}{N}-Ar\underset{\diagdown NO_2}{\diagup X_n} \quad (I)$$

wherein

Ar denotes a mono- or polycyclic aromatic radical having 4 to 16 C atoms, which can also contain 1 to 2 heteroatoms from the series consisting of N, O and S, $R^1$ denotes a mono- or polycyclic aromatic radical having 5 to 16 ring members, which consist of carbon atoms and optionally up to 3 heteroatoms from the series N, O and S, $R^2$ denotes hydrogen, $C_1$–$C_8$-alkyl, $C_2$–$C_8$-alkenyl, $C_3$–$C_7$-cycloalkyl or $C_6$–$C_{14}$-aryl, where these substituents can be substituted 1 to 3 times by halogen, $C_1$–$C_4$-alkyl, amino and/or $C_1$–$C_4$-alkoxy, X denotes halogen, cyano, $C_1$–$C_4$-alkyl, halogenated $C_1$–$C_4$-alkyl, $C_1$–$C_4$-alkoxy, halogenated $C_1$–$C_4$-alkoxy, $C_1$–$C_4$-alkylmercapto, halogenated $C_1$–$C_4$-alkylmercapto, $C_1$–$C_4$-alkylsulphonyl, carboxyl or nitro, n denotes zero, 1, 2 or 3, where if n>1 the substituents X can be different, according to which nitroaromatics of the formula $$Ar\underset{\diagdown NO_2}{\diagup X_n} \quad (II)$$

wherein X, Ar and n have the meanings indicated above, are reacted with amines of the formula $$R^1-\underset{\underset{R^2}{|}}{N}H \quad (III)$$

wherein $R^1$ and $R^2$ have the meanings indicated above, in the presence of bases while introducing oxygen in polar solvents.

2. Process according to claim 1, wherein the base is selected from the group consisting of alkali hydroxide, alkali amide, alkali alkoxide and alkali hydride.

3. Process according to claim 1, wherein the solvent is either a polar aprotic organic solvent or ammonia.

4. Process according to claim 1, wherein the reaction temperature is within the range of from –35° to 120° C.

5. Process according to claim 1, wherein from 0.5 to 10 moles of amine III are used per mol of the nitroaromatic II.

6. Process according to claim 1, wherein the polar solvent is at least one member selected from the group consisting of dimethyl sulphoxide, dimethylformamide, N-methylpyrrolidone, pyridine, dioxane, THF, acetonitrile, sulpholane, dimethyl sulphone and liquid ammonia.

7. Process according to claim 1, wherein the polar solvent comprises liquid ammonia.

8. Process according to claim 1, wherein the polar solvent comprises dimethyl sulphoxide.

* * * * *